United States Patent
Fellows et al.

(10) Patent No.: US 11,241,015 B2
(45) Date of Patent: Feb. 8, 2022

(54) LIQUID ANTIMICROBIAL COMPOSITION

(71) Applicant: GAMA HEALTHCARE LTD, Watford (GB)

(72) Inventors: Adrian Neville Fellows, Watford (GB); Mark James Hallinan, Watford (GB); Dharmit Mistry, Watford (GB)

( * ) Notice: Subject to any disclaimer, the term of this patent is extended or adjusted under 35 U.S.C. 154(b) by 0 days.

(21) Appl. No.: 15/125,264

(22) PCT Filed: Mar. 24, 2015

(86) PCT No.: PCT/GB2015/000099
§ 371 (c)(1),
(2) Date: Sep. 12, 2016

(87) PCT Pub. No.: WO2015/145100
PCT Pub. Date: Oct. 1, 2015

(65) Prior Publication Data
US 2018/0168148 A1    Jun. 21, 2018

(30) Foreign Application Priority Data
Mar. 28, 2014 (GB) .................................. 1405660

(51) Int. Cl.
| | | |
|---|---|---|
| *A01N 47/44* | (2006.01) | |
| *A01N 43/40* | (2006.01) | |
| *A61P 31/04* | (2006.01) | |
| *A61P 17/00* | (2006.01) | |
| *A01N 25/04* | (2006.01) | |
| *A01N 25/30* | (2006.01) | |
| *A01N 37/46* | (2006.01) | |
| *A61K 8/43* | (2006.01) | |
| *A61K 8/88* | (2006.01) | |
| *A61Q 17/00* | (2006.01) | |
| *A61Q 19/10* | (2006.01) | |
| *A01N 33/12* | (2006.01) | |
| *A61K 8/41* | (2006.01) | |

(52) U.S. Cl.
CPC ............ *A01N 47/44* (2013.01); *A01N 25/04* (2013.01); *A01N 25/30* (2013.01); *A01N 33/12* (2013.01); *A01N 37/46* (2013.01); *A01N 43/40* (2013.01); *A61K 8/416* (2013.01); *A61K 8/43* (2013.01); *A61K 8/88* (2013.01); *A61P 17/00* (2018.01); *A61P 31/04* (2018.01); *A61Q 17/005* (2013.01); *A61Q 19/10* (2013.01); *A01N 2300/00* (2013.01); *A61K 2800/51* (2013.01); *A61K 2800/544* (2013.01)

(58) Field of Classification Search
None
See application file for complete search history.

(56) References Cited

U.S. PATENT DOCUMENTS

| | | |
|---|---|---|
| 6,224,898 B1 | 5/2001 | Balogh et al. |
| 6,440,405 B1 | 8/2002 | Cooper et al. |
| 2002/0022012 A1 | 2/2002 | Cooper et al. |
| 2004/0188359 A1 | 9/2004 | King et al. |
| 2005/0048005 A1 | 3/2005 | Stockel |
| 2010/0285148 A1* | 11/2010 | Wlaschin .............. A61M 16/04 424/616 |
| 2014/0018435 A1 | 1/2014 | Hong et al. |

FOREIGN PATENT DOCUMENTS

| | | |
|---|---|---|
| EP | 0271180 A1 | 6/1988 |
| EP | 0858797 A1 | 8/1998 |
| FR | 2867974 A1 | 9/2005 |
| WO | 9714404 A1 | 4/1997 |
| WO | 0015240 A1 | 3/2000 |
| WO | 0072851 A1 | 12/2000 |
| WO | 03024217 A1 | 3/2003 |
| WO | 2005092275 A1 | 10/2005 |
| WO | 2007106437 A2 | 9/2007 |
| WO | 2009088894 A2 | 7/2009 |
| WO | 2013025783 A2 | 2/2013 |

OTHER PUBLICATIONS

Kamel, Amany O., et al. "Preparation of intravenous stealthy acyclovir nanoparticles with increased mean residence time." AAPS PharmSciTech 10.4 (2009): 1427.*
Pubchem entry for "chlorhexidine gluconate" [online], retrieved from the internet on (Jul. 31, 2020) from the URL <https://pubchem.ncbi.nlm.nih.gov/compound/Chlorhexidine-gluconate>.*
Judd, Amy Maryanne. An investigation into the role of dendrimers as potential enhancers of the dermal delivery of topically applied chlorhexidine. Diss. Keele University, 2013.*
International Search Report for corresponding International Application No. PCT/GB2015/000099.
Chen C Z et al: "Recent Advances in Antimicrobial Dendrimers", Advanced Materials, Wiley—V C H Verlag GMBH & Co. Kgaa, DE, vol. 12, No. 11, Jun. 2, 2000 (Jun. 2, 2000), pp. 843-846, XP000963567, ISSN: 0935-9648, DOI: 10.1002/(SICI)1521-4095(200006)12:11<843::AID-ADMA843>3.0.00;2-T p. 844, paragraph 2.—p. 846, paragraph 4.
Aleksandra Felczak et al: "Antimicrobial activity of poly(propylene imine) dendrimers", New Journal of Chemistry, vol. 36, No. 11, Jan. 1, 2012 (Jan. 1, 2012), p. 2215.
Chris Zhisheng Chen et al: "Quaternary Ammonium Functionalized Poly(propylene imine) Dendrimers as Effective Antimicrobials: Structure-Activity Studies", Bi omacromolecules, vol. 1, No. 3, Sep. 1, 2000 (Sep. 1, 2000), pp. 473-480.

* cited by examiner

*Primary Examiner* — John Pak
*Assistant Examiner* — Daniel L Branson
(74) *Attorney, Agent, or Firm* — Egbert, McDaniel & Swartz, PLLC

(57) ABSTRACT

A valve structuring designed for use in all water installations, water inlets for houses, kitchen installations and embedded shower filters as a stop valve, in the areas to perform on-off control, in faucets with the purpose of providing water savings and to use in domestic and industrial type kitchen faucets as a stop valve. The valve is designed for use as an on-off valve in air installations that operate with air.

13 Claims, 1 Drawing Sheet

Figure 1. CHG = Chlorhexidine digluconate, L = L61 Block co-polymer, F1 = First Generation (PAMAM) 0.2%, F2 = First Generation (PAMAM) 0.1%, Z1 = Zero Generation (PAMAM) 0.2%, Z2 = Zero Generation (PAMAM) 0.1%.

Figure 2. CHG = Chlorhexidine digluconate, P or PE = PE 9400 Block co-polymer, F1 = First Generation (PAMAM) 0.2%, F2 = First Generation (PAMAM) 0.1%, Z1 = Zero Generation (PAMAM) 0.2%, Z2 = Zero Generation (PAMAM) 0.1%.

LIQUID ANTIMICROBIAL COMPOSITION

The present invention relates to a liquid antimicrobial composition and in particular to such a composition for use in the disinfection of the skin of a human or animal where disinfection of a drug resistant organism may be required.

There is a need to disinfect skin prior to operations that may breach the skin barrier and permit ingress of micro-organisms that may cause infection. These micro-organisms may be external contaminants from the environment or equipment or may be the normal commensal skin flora, which though harmless in their normal external sites, may cause serious infection inside the body. It is also beneficial to have a means of cleaning and disinfecting the skin of hospital patients who are incapable of bathing or showering.

Many agents have been used on skin for these purposes. In the past chloride of lime and other chlorine donor chemicals were used but these are highly aggressive and damaging to the skin. More recently, agents such as iodophors, povidone iodine, alcohol gels, aqueous chlorhexidine and alcoholic chlorhexidine formulations have been used. Alcohol alone, either as ethanol or propan-2-ol, is an effective skin disinfectant but the effect is short-lived. Alcoholic chlorhexidine is currently a widespread agent of choice because it combines the cationic residual and longer-lasting antimicrobial activity of chlorhexidine with the activity of the alcohol. The combination of 70% alcohol with 2-4% chlorhexidine has been shown to be highly effective and is widely in use around the world, particularly for small surgical site disinfection and disinfection requirements associated with central line and venous catheterisation.

Chlorhexidine and other cationic disinfectants are also widely used in aqueous-based skin care formulations in products such as patient bed bath wipes, pre-operative skin disinfecting products in liquid or wipe presentation, and antiseptic shampoo caps and preparations. Their excellent spectrum of antimicrobial activity combined with good residual activity and relative safety are the major reasons for the success of these products.

However, although a highly effective and beneficial product in health care, it has recently come to the notice of the healthcare community that enhanced resistance and a selection of bacterial strains resistant to chlorhexidine are becoming prevalent. This is a serious problem. Although, the increased level of resistance noted is small in terms of concentration compared to the 2-4% level applied to the skin; this low level increase assumes importance for chlorhexidine because of the overall mode of action which involves prolonged residual activity and the persistent presence on the skin of very low residual concentrations. If bacteria develop enhanced resistance, then the benefit of chlorhexidine's residual activity may be severely compromised. Concerns have also been expressed about increased dermal allergic responses to chlorhexidine and even instances of anaphylaxis caused by chlorhexidine.

Enhanced resistance to chlorhexidine and other cationic biocides is acquired by organisms by way of mutation and selection of those that have a greater effectiveness of their efflux pump mechanism. The efflux pumps are proteins that are encoded by genes such as qacA and cepA and that are embedded in the bacterial cell plasma membrane. Their function is to recognise noxious, potentially damaging agents that have penetrated the cell wall and reached the periplasm or cytoplasm. The efflux pump then extrudes or expels the agent to the external environment before it reaches its target. Efflux pumps are therefore transporters of noxious compounds from within the bacterial cell to the external environment. This achieved by using energy derived from adenosine triphosphate (ATP) or the proton motive force (pmf). So called ABC transporters directly use ATP whilst RND-type efflux pumps use a hydronium ion pH gradient. Efflux pump expression and enhancement can arise from chromosomal mutation or plasmid acquisition. Overexpression of the efflux pump mechanism results in an increased resistance to cell-membrane disrupting antimicrobials and may give rise to multiple drug resistant (MDR) strains of bacteria.

Study of the mechanisms of efflux pumps has given rise to an understanding of their function and subsequently, the means by which their function may be inhibited. Four main mechanisms of efflux pump inhibition have been identified. These are as follows.
1. Reduction of the bacterial cell access to ions such as $Ca2+$, which play cofactor roles in efflux pumps.
2. Inhibition of access to the energy provided by the proton-motive force (pmf).
3. Inhibition of enzymes that provide the hydronium ions required for maintenance of the pmf.
4. Competing with the invading noxious agent for access to the efflux pump, for example by non-specific blocking or coating of the bacterial envelope.

In the clinical context of the provision of topical antiseptic treatment, not all of these approaches to efflux pump inhibition are equally feasible.

Apart from chlorhexidine, other cationic biocides are known that are also membrane-active such that they disrupt and/or penetrate the microbial cell membrane. Examples of these are polymeric biguanides such as polyhexamethylene biguanide (PHMB), polyhexamethylene biguanide hydrochloride, octenidine dihyrochloride and quaternary ammonium compounds. While some of these cationic biocides have not, as yet, shown the development of resistance by the efflux pump mechanism it is thought that inhibition of the efflux pump mechanism with respect to these biocides may also be advantageous.

It is therefore an object of the present invention to provide a liquid antimicrobial composition for use in the disinfection of the skin of a human or animal that maintains the antimicrobial benefit of treating the skin with a cationic, cell membrane-disrupting biocide while removing or mitigating the ability of microorganisms to develop enhanced resistance to it via the efflux pump route.

BRIEF DESCRIPTION OF THE SEVERAL VIEW OF THE DRAWINGS

DETAILED DESCRIPTION OF THE INVENTION

Figure 1:
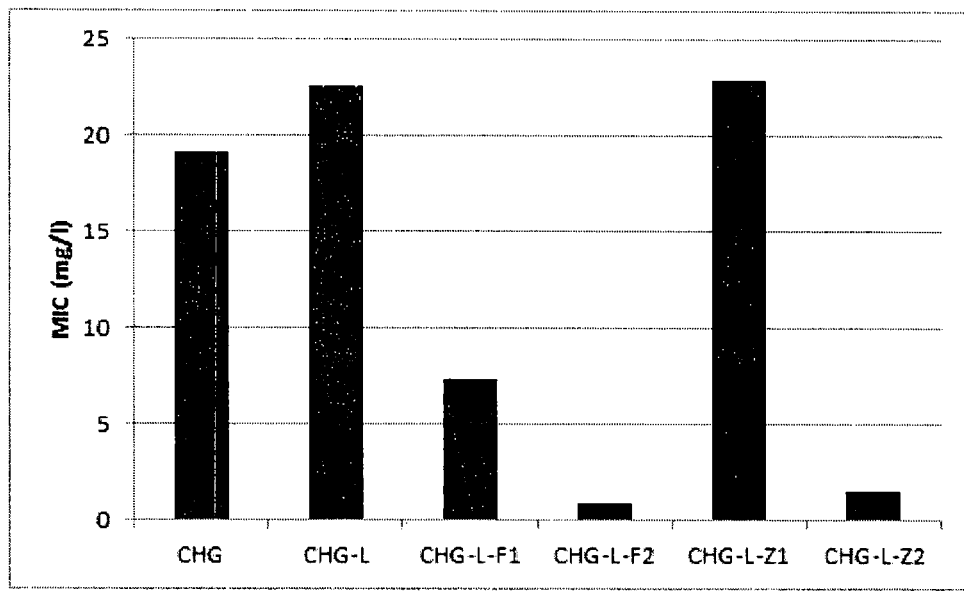
FIG. 1 is a graph showing the MIC test results for formulations comprising chlorhexidine digluconate with and without L61 Block copolymer /PAMAM dendrimer as detailed in the specification.

According to the present invention there is provided a liquid antimicrobial composition for use in the disinfection of the skin of a human or animal comprising a cationic, cell membrane-disrupting biocide and a cationic dendrimer capable of inhibiting an efflux pump mechanism of said cell membrane.

It has been found by the applicant that cationic dendrimers have the ability to bind and disrupt the bacterial membrane thereby inhibiting or destroying the efflux pump mechanism. The addition of a dendrimer to the composition also enhances the antiviral property of the composition. Such dendrimers need not be biocides sufficient to meet regulatory requirements in their own right but owing to their capability to inhibit the efflux pump mechanisms of microbial cell membranes they significantly reduce the ability of the microorganism to develop an enhanced resistance to the cationic, cell membrane-disrupting biocide used in the composition along with it.

Preferably also, the cationic, cell membrane-disrupting biocide comprises any or a combination of chlorhexidine, a polymeric biguanide, octenidine dihydrochloride and a quaternary ammonium compound.

Preferably, the cationic, cell membrane-disrupting biocide is chlorhexidine in the form of a gluconate or of an acetate salt. Advantageously, the chlorhexidine is present in the composition in a concentration between 0.25% and 6.00% w/v inclusive. Such a concentration is one suitable for use in topical disinfectants for use on the skin of humans and animals.

Dendrimers are repetitively branched molecules that are typically symmetric around a core. They can be synthesized with a wide range of physicochemical properties by controlling the core group, branching and the nature and number of functional groups on the surface. There are many variations which may be of value in this invention.

Dendrimers are also classified by generation, which refers to the number of repeated branching cycles that are performed during its synthesis. Each successive generation results in a dendrimer roughly twice the molecular weight of the previous generation. Lower generation dendrimers, classified as generation 0 to generation 2 dendrimers (G0-G2), are flexible molecules with no appreciable inner regions while medium sized generation 3 (G-3) and generation 4 (G-4) dendrimers generally have an internal space that is separated from the outer shell of the dendrimer. Very large generation 7 (G-7) and greater dendrimers are more like solid particles with very dense surfaces due to the structure of their outer shell. Higher generation dendrimers also have more exposed functional groups on the surface, which enables them to be customized for a given applications.

In the present invention, generation 0 to generation 3 dendrimers, and more preferably generation 0 to generation 2 dendrimers, are preferred as they form flat, so called "starfish" conformations and it has been found that these are more effective in disrupting the efflux pump mechanisms or microorganisms than generation 4 and above dendrimers.

The dendrimer may be quaternary ammonium functionalised poly(propyleneimine), polylysine and dendrimers with surface groups based on sugars, for example mannose or maltose. Other types of dendrimer of value in the invention include poly(amidoamine) or PAMAM dendrimers, particularly those with surface amino groups. Poly(amidoamine), or PAMAM dendrimers have a core that is a diamine, usually ethylenediamine, which is reacted with methyl acrylate and then another ethylenediamine to make the generation 0 (G-0) PAMAM. Successive reactions create higher generations.

As large molecule dendrimers generally produce solutions of low viscosity relative to the size of the molecule, preferably the composition comprises the dendrimer in a range of between 0.01% w/v and 2% w/v inclusive. This is range is particularly advantageous when the composition comprises a 2% to 4% chlorhexidine solution.

Preferably, the composition is an aqueous or aqueous alcohol solution, dispersion or emulsion, for example using isopropyl alcohol.

The composition may also comprise surfactants to provide cleaning and wetting properties, solvents with biocidal properties such as alcohols and chelating agents, where use in hard waters may be an issue. Emollients and skin conditioning chemicals may also be added to the composition, for example tocopheryl acetate. Preservatives such as benzalkonium chloride and/or citric acid may also be added in appropriate quantities.

The surfactant preferably comprises between 0.05% w/v and to 5.00% w/v inclusive of the composition. Suitable surfactants are those characterised as di block or tri block copolymers of ethylene oxide and propylene oxide, for example poly(ethylene oxide)-b-(propylene oxide)-b-(ethylene oxide), that is PEO-PPO-PEO block copolymers, terminating in hydroxyl groups. These are manufactured, for example, by BASF Corporation and sold under their registered trade mark Pluronic®. A suitable surfactant this company would be that sold under their trade mark Pluronic® P85. These block copolymer surfactants may be utilised alone as a single molecular weight product, chosen for example from copolymers such as poloxamers, or as a combination of two or more such surfactants. Other suitable surfactants are polyethylene glycols (PEG), for example PEG 40. Such single or combination surfactants may in turn be combined with other types of surfactant, for example glucoside, polyglucoside, linear chain alcohol ethoxylates and the like. Nonionic surfactants are particularly preferred.

In addition, preferably a significant proportion of the surfactant has a hydrophilic-lipophilic balance (HLB) with a value between 10 and 17 inclusive. Such surfactants are water soluble and those with HLB values above 12 act as oil in water emulsifiers. This is advantageous if the composition is an aqueous solution and formulated to include an essential oil or essential oil component as the surfactant, for example polyethylene glycol, will act to disperse the essential oil throughout the solution.

Wetting agents such as polylsorbate 20 and non-ionic, foaming surfactants such caprylyl/decyl glucoside may also be added to the composition.

In formulations of the composition that are aqueous or aqueous alcoholic solutions, the formation of micelles by the surfactant is not desirable as this would decrease the composition's efficacy as an efflux pump inhibitor. Hence, preferably the surfactant is present at a concentration that is below its critical micelle concentration. Advantageously, the surfactant is present at a concentration that is at least 10% below its critical micelle concentration.

In addition, natural and synthetic polycations may play a useful role in compositions of the present invention. Examples are synthetic polycations such as poly(allylamine) hydrochloride, poly hexamethylene biguanide hydrochloride, poly(diallylmethyl ammonium) chloride, poly(ethyleneimine), and polyvinylpyrollidone. Examples of natural polycations are poly-L-ornithine, poly-L-arginine, protamines and chitosan.

Chelating agents such as etidronic acid (1-hydroxyethane 1,1-diphosphonic acid (HEDP)), ethylene diamine, di or tetra acetate, phosphonates, nitriloacetates or others may also be included in the composition as may essential oils or selected essential oil components. Preferably, the chelating agent is present in a range of 0.05% w/v to 1.00% w/v inclusive of the composition.

As indicated above, preferably the essential oil or essential oil component is included along with a suitable solvent that will disperse it throughout the composition. Suitable solvents include ethanol and polyethylene glycol, which may also be present as a surfactant as indicated above. The essential oil or essential oil component preferably comprises between 0.01% w/v and 1.00 w/v % inclusive of the composition.

Compositions in accordance with the present invention as described above minimize the risk of antimicrobial resistance to the cationic, cell membrane-disrupting biocide in the composition developing. The dendrimer interacts with the cell membranes of the microorganisms and gives rise to a decrease in microviscosity. In mammals it has been noted that this is accompanied by inhibition of P-glycoprotein activity. It has been found that similar effects occur in bacteria where the structure of the ABC efflux transporter is similar to the P-glycoprotein (P-gp). Strong energy depletion, inhibition of efflux proteins and subsequent ATP depletion causes a closedown of the drug efflux systems allowing increase of biocide input; essentially a sensitisation of the organism to the biocide.

Interference with the transporter mechanism can be assayed by both membrane ATPase assay and cellular calcein assays. Porin expression can also be assayed by the ethidium bromide or acridine orange techniques allowing assessment of the efficacy of particular formulations and their relevance to individual aspects of patient care. It is also the case that inhibition of the efflux pump mechanism will also beneficially impact on biofilm production and quorum sensing by the microbial population. This will further improve the efficacy of biocides in formulations covered by this invention.

Other compounds may also be suitable for inclusion in specific formulations of the invention. In particular, compounds that may also inhibit the efflux pump mechanism. These may be drawn from various chemical groups, including phenothiazine neurologically active drugs, certain essential oils and essential oil components such as berberine, that of *Helichrysum italicum*, geraniol, pinenes, alpha zingiberine, terpenes, tea tree oil and others as well as some complex surface active agents.

In order to prove the effectiveness of the use of dendrimers in inhibiting the efflux pump mechanisms of resistant microorganisms, the minimum inhibitory concentration (MIC) of chlorhexidine digluconate against a chosen bacterium was assessed and then compared to chlorhexidine digluconate formulations that include cationic dendrimers. The method adopted was a double dilution (50% dilution) turbidity method for MIC determination. The test was conducted using the BioScreen® C and subsequent software of Thermo Labsystems, Inc., which analyses 2×100 wells in an incubated spectrophotometer. Double dilutions of chlorhexidine digluconate were prepared in the well with or without the addition of various cationic dendrimers in various combinations along with the chosen bacteria. The minimum inhibitory concentrations were determined by optical density at regular time intervals for a period of 24 hours with the micro-plates incubated at 37° C.

The bacterium chosen for the tests was *Pseudomonas aeruginosa* because its genome includes the required gene (cepA). The test protocol was adopted because it was able to test multiple formulations at once. Therefore, the method was able to compare the chlorhexidine digluconate control against formulations that included cationic dendrimers when treated with the same conditions.

Initial tests were conducted to determine the MIC of chlorhexidine digluconate alone as well as negative controls and eliminate potential interferences of other chemical ingredients in the formula. No significant difference was observed between chlorhexidine digluconate alone and the chlorhexidine digluconate containing formulations that excluded cationic dendrimers. It can be seen that the best results were obtained using a combination of chlorhexidine digluconate, a dendrimer and a block copolymer. However, although the tests demonstrate the effectiveness of the dendrimer and dendrimer block copolymer formulations not all formulations are equally effective.

Figure 2:
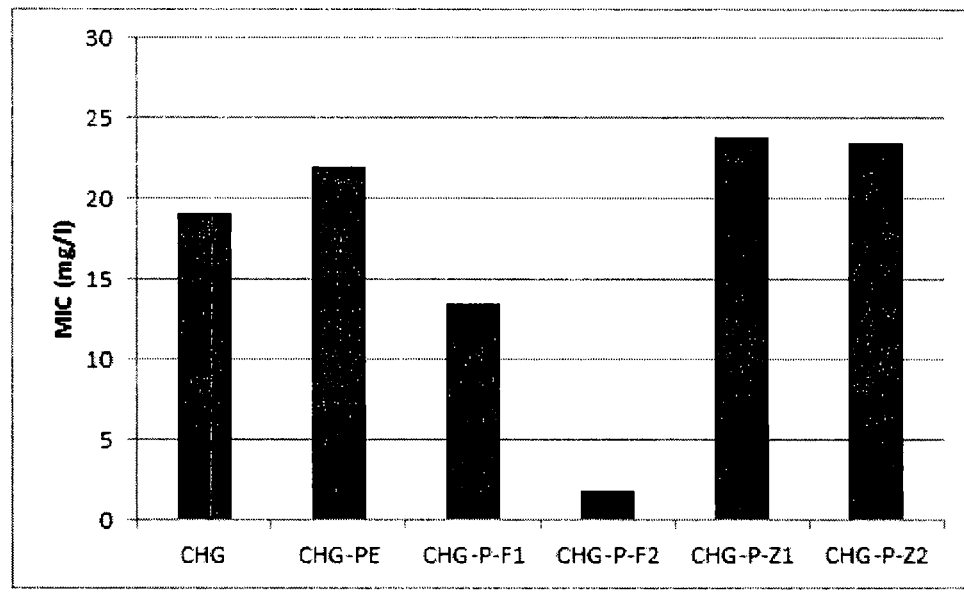
FIG. 2 is a graph showing the MIC test results for formulations comprising chlorhexidine digluconate with and without PE 9400 Block co-polymer/PAMAM dendrimer as detailed in the specification.

The four formulations tested are listed below, two being aqueous solutions and two aqueous alcohol solutions. The chlorhexidine digluconate concentrations were double diluted. In the formulations, only the block copolymers and dendrimer were unchanged, that is they were not diluted. The test results are shown graphically in the accompanying drawings, wherein the graphs in FIGS. 1 and 2 are the MIC results for of chlorhexidine digluconate alone and when combined with cationic dendrimers. The four formulations used in the tests were as follows, 1. Zero Generation (G-0) Dendrimer

| Ingredient | % w/v |
| --- | --- |
| *Isopropyl alcohol (*% v/v) | 70 |
| Chlorhexidine gluconate | 2.5 |
| Block copolymer (Pluronic PE9400 or Pluronic L61) | 0.01 |
| PAMAM Dendrimer (0-G) | 0.1 or 0.2 |
| Water | To 100 ml |

2. Zero Generation (G-0) Dendrimer

| Ingredient | % w/v |
| --- | --- |
| Chlorhexidine gluconate | 2.0 |
| Propylene glycol | 0.50 |
| Tocopheryl acetate | 0.03 |
| Fragrance | 0.10 |
| Polylsorbate 20 | 0.50 |
| Caprylyl/Decyl glucoside | 0.10 |
| Benzalkonium chloride | 0.04 |
| Block copolymer (Pluronic PE9400 or Pluronic L61) | 0.01 |
| PAMAM Dendrimer (0-G) | 0.1 or 0.2 |
| Citric acid | To pH 5.5 |
| Water | To 100 ml |

3. First Generation (G-1) Dendrimer

| Ingredient | % w/v |
| --- | --- |
| Chlorhexidine gluconate | 2.0 |
| Propylene glycol | 0.50 |
| Tocopheryl acetate | 0.03 |
| Fragrance | 0.10 |
| Polylsorbate 20 | 0.50 |
| Caprylyl/Decyl glucoside | 0.10 |
| Benzalkonium chloride | 0.04 |
| Block copolymer (Pluronic PE9400 or Pluronic L61) | 0.01 |
| PAMAM Dendrimer (1-G) | 0.1 or 0.2 |
| Citric acid | To pH 5.5 |
| Water | To 100 ml |

4. First Generation (G-1) Dendrimer

| Ingredient | % w/v |
| --- | --- |
| *Isopropyl alcohol (*% v/v) | 70 |
| Chlorhexidine gluconate | 2.5 |
| Block copolymer (Pluronic PE9400 or Pluronic L61) | 0.01 |
| PAMAM Dendrimer (1-G) | 0.1 or 0.2 |
| Water | To 100 ml |

Apart from the test formulations above, other preferred examples of formulations of antimicrobial compositions in accordance with the present invention are as follows.

EXAMPLE 1

| | |
| --- | --- |
| Chlorhexidine gluconate | 2.00% w/v |
| PEO-PPO-PEO block copolymer | 1.00% w/v |
| Polypropylenimine (PPI) dendrimer | 0.01% w/v |
| Disodium ethylenediaminetetraacetic acid (Disodium EDTA) | 0.05% w/v |
| Water | to 100% |

EXAMPLE 2

| | |
| --- | --- |
| Chlorhexidine gluconate | 2.00% w/v |
| Polypropylenimine (PPI) dendrimer | 1.00% w/v |
| PEO-PPO diblock copolymer | 0.05% w/v |
| HEDP | 0.02% |
| Ethanol | 70% |
| Water | to 100% |

EXAMPLE 3

| | |
| --- | --- |
| Chlorhexidine gluconate | 4.00% w/v |
| Geraniol | 1.00% w/v |
| Polylysine dendrimer | 0.05% w/v |
| Polyhexamethylene biguanide hydrochloride | 0.50% w/v |
| Phenoxyethanol | 0.20% w/v |
| PEG 40 | 0.50% w/v |
| Water | to 100% |

EXAMPLE 4

| | |
| --- | --- |
| Benzalkonium chloride | 1.00% w/v |
| Cetylpyridinium chloride | 0.50% w/v |
| Cationic dendrimer | 1.00% w/v |
| Capryl glucoside surfactant | 0.05% w/v |
| PEO/PPO block copolymer surfactant | 0.50% w/v |
| Water | to 100% |

EXAMPLE 5

| | |
| --- | --- |
| Octenidine dihydrochloride | 2.00% w/v |
| PAMAM dendrimer | 1.00% w/v |
| Polysorbate 20 | 0.50% w/v |
| Glycerine | 1.00% w/v |
| *Aloe vera* | 0.50% w/v |
| Essential oil based fragrance | 0.10% w/v |
| EDTA di sodium salt | 0.05% w/c |
| Water | to 100% |

EXAMPLE 6

| | |
| --- | --- |
| Chorhexidine gluconate | 2.5% w/v |
| Isopropyl alcohol | 70.0% w/v |
| Polypropyleneimine dendrimer | 1.5% w/v |
| Phenoxyethanol | 0.2% w/v |
| Water | to 100% |

It will be appreciated that formulations suitable for human skin application may include further conventional ingredients such as emollients, fragrances, and skin conditioning agents dependent on the properties desired in addition to disinfection. Such formulations are suitable for use as surgical scrubs, cleansers for skin wounds, preoperative skin preparations, germicidal hand rinses and the like. In all cases the cationic membrane-disrupting biocide is preferably present in a concentration between 0.25% w/v and 6.00% w/v inclusive. Other similar applications include those in veterinary medicine and animal husbandry, for example in dairy hygiene products, particularly pre-milking hygiene preparations and teat dips.

The composition of the present invention may be used in combination with a wipe, for example a wipe of woven, knitted or nonwoven material, a sponge and a composite material, for example as a shampoo cap for convenient use. Suitable wipes may be made of any or a mixture of polyolefin, polyester, viscose, cotton, cellulose or other fibres. Sponge wipes may be made of polyurethane. The composition may be adsorbed by such a composite, wipe or sponge, which may be then be packaged ready to be dispensed from a tub, a bucket, a flow-wrap pack or an individually sealed wrapper or sachet.

The invention claimed is:

1. A liquid antimicrobial composition for use in the disinfection of skin of a human or an animal, the liquid antimicrobial composition having a pH of no less than 5.5 and being an aqueous or aqueous alcohol solution or dispersion, the liquid antimicrobial composition comprising:
   a cationic cell-membrane biocide having chlorhexidine of a gluconate or an acetate salt form that is present in a concentration of between 0.25% and 6.00% w/v inclusive;
   a cationic dendrimer capable of inhibiting an efflux pump mechanism of a cell membrane that is present in a concentration of between 0.01% and 2.0% w/v inclusive of the antimicrobial composition, said cationic dendrimer being a generation 0 to generation 1 polyamidoamine dendrimer; and
   a non-ionic surfactant that is present at a concentration at least 10% below a critical micelle concentration thereof.

2. The liquid antimicrobial composition of claim 1, said surfactant is a poloxamer tri block copolymer surfactant.

3. The liquid antimicrobial composition of claim 1, wherein said non-ionic surfactant has a hydrophilic-lipophilic balance (HLB) of between 10 and 17 inclusive.

4. The liquid antimicrobial composition of claim 1, wherein said non-ionic surfactant is between 0.05% w/v and 5.00% w/v inclusive of the liquid antimicrobial composition.

5. The liquid antimicrobial composition of claim 1, further comprising:
a chelating agent.

6. The liquid antimicrobial composition of claim 5, wherein said chelating agent is any or a combination of etidronic acid (1-hydroxyethane 1,1-diphosphonic acid (HEDP)), ethylene diamine, di or tetra acetate, a phosphonate and a nitriloacetate.

7. The liquid antimicrobial composition of claim 5, wherein said chelating agent is between 0.05% w/v and 1.00% w/v inclusive of the liquid antimicrobial composition.

8. The liquid antimicrobial composition of claim 1, further comprising:
an essential oil or essential oil component in combination with a solvent.

9. The liquid antimicrobial composition of claim 8, the solvent being ethanol or polyethylene glycol.

10. The liquid antimicrobial composition of claim 8, wherein said essential oil or essential oil component is any or a combination of berberine, *Helichrysum italicum*, geraniol, a pinene, alpha zingiberine, a terpene and tea tree oil.

11. The liquid antimicrobial composition of claim 8, wherein said essential oil or essential oil component is between 0.01% w/v and 1.00% w/v inclusive of the liquid antimicrobial composition.

12. The liquid antimicrobial composition of claim 1, wherein the liquid antimicrobial composition is combined with a wipe, a sponge or a shampoo cap.

13. A method of disinfecting skin of a human or an animal, the method comprising:
applying a liquid antimicrobial composition having a pH no less than 5.5 to the skin of a human or an animal, wherein the liquid antimicrobial composition is an aqueous or aqueous alcohol solution or dispersion and comprises:
a cationic cell-membrane biocide having chlorhexidine of a gluconate or an acetate salt form that is present in a concentration of between 0.25% and 6.00% w/v inclusive;
a cationic dendrimer capable of inhibiting an efflux pump mechanism of a cell membrane that is present in a concentration of between 0.01% and 2.0% w/v inclusive of the antimicrobial composition; said cationic dendrimer being a generation 0 to generation 1 polyamidoamine dendrimer; and
a non-ionic surfactant that is present at a concentration at least 10% below a critical micelle concentration thereof.

* * * * *

UNITED STATES PATENT AND TRADEMARK OFFICE
CERTIFICATE OF CORRECTION

| | |
|---|---|
| PATENT NO. | : 11,241,015 B2 |
| APPLICATION NO. | : 15/125264 |
| DATED | : February 8, 2022 |
| INVENTOR(S) | : Adrian Neville Fellows, Mark James Hallinan and Dharmit Mistry |

It is certified that error appears in the above-identified patent and that said Letters Patent is hereby corrected as shown below:

On the Title Page

Item (57) Abstract should read as follows:
A liquid antimicrobial composition is provided for use in the disinfection of the skin of a human or an animal, in particular where disinfection of a drug resistant organism is required. The composition includes a cationic, cell membrane-disrupting biocide and a cationic dendrimer capable of inhibiting an efflux pump mechanism of the cell membrane. The biocide is preferably any or a combination of chlorhexidine, a polymeric biguanide, octenidine dihydrochloride and a quaternary ammonium compound. The dendrimer binds and disrupts the cell membranes of microorganisms in order to inhibit or destroy the cell's efflux pump mechanism thereby preventing microorganism strains resistant to the biocide from becoming prevalent, particularly if the biocide includes chlorhexidine. The dendrimer is preferably a G-0 to G-3 dendrimer being any or a combination of quaternary ammonium functionalised poly(propylene imine), polylysine, dendrimers with surface groups based on a sugar and polyamide amine (PAMAM) dendrimers.

Signed and Sealed this
Twentieth Day of September, 2022

*Katherine Kelly Vidal*

Katherine Kelly Vidal
*Director of the United States Patent and Trademark Office*